United States Patent [19]

Petersen

[11] 4,260,803

[45] Apr. 7, 1981

[54] CHLOROMETHYLBENZOIC ACID ESTERS OF PHENOLS

[75] Inventor: Egon N. Petersen, Neunkirchen-Seelscheid, Fed. Rep. of Germany

[73] Assignee: Dynamit Nobel Aktiengesellschaft, Cologne, Fed. Rep. of Germany

[21] Appl. No.: 53,886

[22] Filed: Jul. 2, 1979

Related U.S. Application Data

[63] Continuation of Ser. No. 804,837, Jun. 8, 1977, abandoned, which is a continuation of Ser. No. 619,351, Oct. 3, 1975, abandoned.

[30] Foreign Application Priority Data

Oct. 4, 1974 [DE]  Fed. Rep. of Germany ....... 2447385

[51] Int. Cl.$^3$ ............................................. C07C 69/773
[52] U.S. Cl. .............................. 560/108; 260/45.85 B; 260/455 R; 260/941; 546/174; 560/65; 560/109; 424/308
[58] Field of Search ............................. 560/108, 109

[56] References Cited

U.S. PATENT DOCUMENTS

| | | | |
|---|---|---|---|
| 3,359,302 | 12/1967 | Medley et al. ........................ | 560/86 |
| 3,609,167 | 9/1971 | Zirkle ................................... | 560/109 |
| 4,068,082 | 1/1978 | Stoffey et al. ........................ | 560/108 |

FOREIGN PATENT DOCUMENTS 1191270  5/1970  United Kingdom ..................... 560/109

OTHER PUBLICATIONS

Weygand et al., *Preparative Organic Chemistry*, pp. 378–379 (1972).

*Primary Examiner*—Jane S. Myers
*Attorney, Agent, or Firm*—Sprung, Felfe, Horn, Lynch & Kramer

[57] ABSTRACT p- and o-chloromethylbenzoic acid phenyl esters and thiophenyl esters of the formula

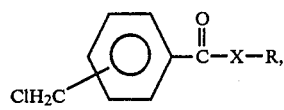

I wherein X represents oxygen or sulfur and R the radical of a mononuclear or polynuclear phenol or thiophenol which is unsubstituted or which bears additional substituents which may include the substituent

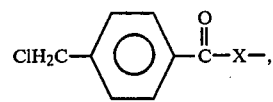

wherein X is as above. The components can be produced by reacting p- or o-chloromethylbenzoyl chloride with univalent or polyvalent, mononuclear or polynuclear phenols or the thiophenols in the presence of inert solvents and tertiary amines in a catalytic or stoichiometric amount, amides in a catalytic amount, or in an aqueous alkaline medium.

8 Claims, No Drawings

CHLOROMETHYLBENZOIC ACID ESTERS OF PHENOLS

This is a continuation of application Ser. No. 804,837, filed June 8, 1977, now abandoned, which is a continuation of application Ser. No. 619,351, filed Oct. 3, 1975, now abandoned.

Chloromethylbenzoic acid esters of phenols, substituted phenols and the corresponding thiophenols have not yet been described in the literature.

The present invention relates to the new esters and to methods for the preparation of these esters by the reaction of chloromethylbenzoyl chlorides with the corresponding phenols or thiophenols or their alkali salts.

The subject matter of the invention, therefore, is p- and o-chloromethylbenzoic acid phenyl esters and thiophenyl esters of the formula

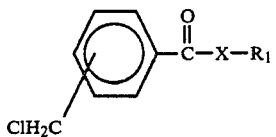

I wherein X represents oxygen or sulfur and R the radical of a mononuclear or polynuclear phenol or thiophenol which is unsubstituted or which bears additional substituents including the substituent

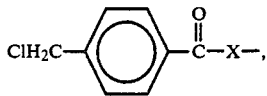

In the case of the univalent phenols or thiophenols, the new compounds are monoesters, and in the case of the bivalent phenols or thiophenols they are bisesters with two chloromethylbenzoic acid groups.

Where the esters of thiophenols are involved, they can also be understood as chloromethylbenzoic acid thiol esters.

The radicals of mononuclear phenols and thiophenols are to be based especially on the benzene ring, although other five-member and six-member carbon rings and heterocyclic rings are possible.

The radicals of polynuclear phenols and thiophenols can be of many different kinds.

In the case of condensed rings, the preferred carbocyclic ring is the naphthaline ring and the preferred heterocyclic ring is the quinoline ring, although other rings, such as the anthracene ring, are possible.

In the case of the noncondensed systems, the preferred ring joined by a single bond is the radical of diphenyl, while the preferred rings joined by atomic groups are the benzene rings, the bond being able to be through hydrocarbon radicals such as, for example, a methylene group, a dialkylmethylene group, a chalcogenic atom such as an oxygen or sulfur atom, preferably the group $-SO_2-$, and other bonds being possible.

In the case of radicals R which are bifunctional due to the presence of the substituents

these radicals can be derived from mononuclear, bifunctional phenols, such as hydroquinone, resorcinol, pyrocatechol, or, for example, the alkyl homologues thereof, or from polynuclear diphenols such as p,p'-dihydroxydiphenyl, or condensed aromatic ring systems, those of diphenols with isolated aromatic nuclei having intermediate atoms or atom groups being of particular interest, these being formulated as

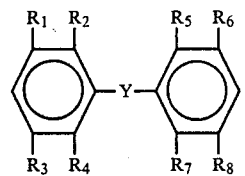

wherein the group Y is a straight or branched hydrocarbon radical of preferably 1 to 4 carbon atoms, such as a methylene group or dialkylmethylene group, or O, S or $SO_2$ groups, as well as other possible intermediate groups, and $R_1$ to $R_8$ can be identical or different substituents from among those named hereinbelow, or hydrogen.

In the radicals of the mononuclear or polynuclear phenols and thiophenols the free ring positions can bear additional substituents, one or several or even a relatively great number or all of the free ring positions having the same or different substituents.

Preferred substituents are:

Alkyl radicals, especially low alkyl groups of 1 to 6 carbon atoms, such as methyl, ethyl-propyl and isopropyl, butyl and tertiary butyl groups;

Aromatic radicals, especially the phenyl group and substituted phenyl groups;

Araliphatic radicals, especially the benzyl group;

Alkoxy radicals, especially those of 1 to 4 carbon atoms, such as methoxy, ethoxy and butoxy groups;

Aroxy radicals, especially the phenoxy group;

Aralkoxy radicals, especially the benzyloxy group;

Halogen radicals, especially chlorine and bromine substituents, or also

Nitro groups, other radicals also being possible, such as carbonyl, carboxyl or carboxyester groups.

Accordingly, the nature of the possible substituents is essentially unlimited, so that only substituents reacting with the phenolic OH group or the acid chloride group, such as for example unshielded (free) primary or secondary amines, and substituents which hydrolyze in method of procedure B (see below), are less desirable.

Additional subject matter of the invention is a method of preparing esters of Formula I, which is characterized in that p- or o-chloromethylbenzoyl chloride is made to react with univalent or polyvalent, mononuclear or polynuclear, unsubstituted or substituent-bearing phenols or the thiophenols corresponding thereto, in the presence of inert solvents and tertiary amines in a catalytic or stoichiometric amount, or amides in a catalytic amount, or in an aqueous, alkaline medium.

The isomeric chloromethylbenzoyl chlorides representing the one reaction component, are easily accessible compounds.

For example, p-choromethylbenzoyl chloride can be prepared from p-toluylic acid by transformation to the acid chloride and the single-stage chlorination of the side chain thereof. Such processes are described, for example, in German Reich Patent No. 239,311, by Blicke and Lilienfeld in Am. Chem. Soc. 65 (1943) 2281, 2282, and also by Titley in Chem. Soc. (London) (1928) 2582, and in Ch.Z. 25 (1901) 793.

Since especially p-toluylic acid occurs as a by-product in the oxidation of p-xylene to terephthalic acid on a large technical scale, and the same circumstances prevail in the oxidation of o-xylene to phthalic acid on a large technical scale, an inexpensive starting material is thus available in sufficient amounts.

The process is performed generally in the temperature range from 0° C. to 150° C., although it can also be performed at higher or lower temperatures as well. If gaseous hydrogen chloride is evolved, a process at atmospheric pressure is greatly preferred, and if sufficient amounts of bases or HCl-adsorbing substances are present, the reaction can also be performed under pressure, for example at pressures up to about 10 atmospheres.

The reactants are used in equivalent amounts, excesses of one component being also possible, such as for example a 10% excess, so that in the case of monoesters the molar ratio of phenol or thiophenol, as the case may be, to acid chloride amounts to approximately 1:1 and in the case of bisesters to about 1:2.

Three methods of reaction are possible, which differ slightly with respect to the adjuvants and the reaction media:

(A) Reaction of the chloromethylbenzoic acid chloride with the phenol in inert solvents in the presence of stoichiometric amounts of a tertiary amine as hydrogen chloride interceptor.

(B) Reaction of the Schotten-Baumann type in an aqueous alkaline medium.

(C) Reaction of the starting components in inert solvents with catalytic amounts of tertiary amines or amides at elevated temperatures.

With regard to methods A and C, a substantially water-free reaction medium is necessary or desirable, so that, in general, dried or absolute solvents are used in a dry apparatus which is protected by means of a drying tube, and which is rinsed if necessary with dry gases such as nitrogen.

In these cases the reactants are also dried prior to the reaction.

The inert solvents can be any of a great number of solvents which do not participate in the reaction, the preferred ones being aromatic hydrocarbons such as benzene, toluene or xylene, cyclic ethers such as tetrahydrofuran, and benzine fractions such as petroleum ether or ligroin.

Suitable hydrogen chloride interceptors or catalysts are tertiary amines such as pyridine, N-methylpyrrolidine or tertiary butylamine, as well as amines such as N-methylpyrrolidone, dibutylformamide or N,N-dibutylacetamide. If the reaction is performed in an aqueous-alkaline medium, alkali lyes, such as aqueous soda lye or potash lye are present in an amount approximately equivalent to the amount of HCl being formed. The phenols or thiophenols can be dissolved in the lye prior to the reaction.

It is surprising that, in the present process, it is exclusively the acid chloride group of the chloromethylbenzoyl chlorides that enters the reaction in a high yield, while the chloromethyl group that is present remains virtually unchanged. Any reaction or partial reaction of the $ClCH_2$ group that might be expected does not take place.

In addition, it was not foreseeble that, in all three of the above-named procedures, the reaction produces, in a high yield, exclusively the chloromethylbenzoic acid esters, in good purity, and with virtually no secondary reactions of the $ClCH_2$ group.

The phenols or thiophenols can be univalent or polyvalent. Suitable phenols and thiophenols include monophenols and monothiophenols such as phenol, alkylphenols such as o-, m- and p-cresol, the isomeric xylenols, i-propylphenols, thymol, the cumylphenols, o-, m- and p-nitrophenols, and the isomeric dinitrophenols, isomeric aminophenols or aminonaphthols shielded at the amino group, o-, m- and p-chlorophenol, the isomeric dichlorophenols, trichlorophenols, tetrachlorophenols and pentachlorophenol, as well as the mono- to pentabromophenols corresponding to these chlorophenols, and mixed chlorobromophenols, phenol ethers such as o-, m- and p-methoxyphenols, ethoxyphenols, propoxyphenols and dimethoxyphenols, the isomeric phenoxyphenols and benzyloxyphenols, as well as the half-ethers of the diphenols named below, phenols with mixed substituents such as dichloromethylphenols, chlorodimethylphenols and dichlorodimethylphenols, and the bromoalkylphenols, phenols of polynuclear carbocyclic or heterocyclic rings such as $\alpha$- and $\beta$-naphthol and 8-hydroxyquinoline and, to the same extent, the monothiophenols corresponding to the above-named monophenols, as well as polyvalent phenols such as pyrocatechol, resorcinol, hydroquinones and their alkyl and chloro substitution products, as well as pyrogallolmono- or -bisalkyl ether and phloroglucine monoalkyl or bisalkyl ether, the isomeric dihydroxydiphenyls or their substitution products, such as alkyl-substitution products or halogen substitution products, the isomeric dihydroxy derivatives of diphenyl ether, and diphenyl sulfide and diphenylsulfone—the latter being commonly referred to as thiodiphenols and sulfonyldiphenols, respectively—and their substitution products.

Bilateral bis-(hydroxyphenyl) derivatives of alkanes, such as dihydroxy-(diphenylmethane) or dihydroxydiphenylethane, dihydroxydiphenylpropane and dihydroxydiphenyl-1-propane, the latter known as bisphenol A, and especially their chloro and bromo substitution products, and also the dithiophenols corresponding to these diphenols.

The esters prepared are, as it has already been stated, reactive and in some cases highly reactive compounds, which are capable of another reaction at the $ClCH_2$ group and, in some cases, at other substituents.

Accordingly, the products prepared are used especially as intermediates for a number of further syntheses, it being possible through the selection of the compound that is to react with the $ClCH_2$ group (in connection also with the nature and the substituents of the phenolic or thiophenolic group) to achieve certain characteristics, such as, for example, biological activity in the form of herbicides or germicides, or antimycotic properties, for example through a greater number of chlorine or bromine substituents or of phosphorous groups.

In addition, the products can be used directly, for example as antioxidant additives for plastics, or, if they contain a number of halogen atoms, as sterilizing substances or antifouling agents.

EXAMPLES

EXAMPLE 1 p-Chloromethylbenzoic acid phenyl ester

By Method C:

In a four-necked, round flask of a capacity of 250 ml, equipped with stirrer, reflux condenser, internal thermometer and a dropping funnel, 47 g (0.5 mole) of anhydrous phenol and 50 ml of absolute benzene were placed with the exclusion of moisture; 0.5 ml of absolute pyridine was added to the solution and the solution was heated to 50° C. At this temperature, a solution of 95 g (0.5 mole) of 99% pure p-chloromethylbenzoyl chloride (M.P. 26.5°–28° C.) in 80 ml of benzene was added drop by drop over a period of 10 minutes. HCl immediately began to evolve. The temperature of the reaction mixture was left between 50° and 55° C. for 30 minutes, and then, for completion of the reaction, the mixture was refluxed for another 5 hours, while a weak current of nitrogen gas was passed through the apparatus.

The solvent benzene was substantially removed from the clear, light yellow reaction solution, at first under normal pressure, and finally in a water-jet vacuum. The residue in the flask crystallized on cooling to a yellowish-white crystal cake whose weight amounted to 123 g, corresponding to a virtually 100% yield. Melting point of the raw product: 74°–82° C. The raw product was recrystallized from 1.6 liters of cyclohexane. We obtained colorless, pearly flakes of a melting point of 85° to 86.5° C. 20 g of the substance was again recrystallized from 300 ml of cyclohexane for analysis. There was no further change in the melting point.

Elemental Analysis: $C_{14}H_{11}ClO_2$ (Mol. Wt=246.7).
Calculated: C 68.17%; H 4.49%; Cl 14.37%; O 12.97%.
Found: C 67.98%; H 4.33%; Cl 14.31%; O 13.10%.

The structure of the ester was confirmed by infrared and nuclear magnetic resonance testing.

By Method B:

In a glass beaker, 18.8 g (0.2 mole) of phenol was dissolved in 200 ml of normal caustic soda solution, and to this phenolate solution 38 g (0.2 moles) of p-chloromethylbenzoyl chloride, liquefied by heating, was added, drop by drop, with stirring, at 20° to 25° C., over a period of 30 minutes. Immediately an unctuous, clotted, colorless product precipitated. The reaction was allowed to continue for 1 hour at room temperature, with stirring, the precipitated reaction product was removed by suction filtration, and washed neutral with water. After drying, 35 g was obtained, corresponding to 71% of the theoretically possible yield. The raw product was purified by recrystallization from cyclohexane. Thereafter it melted at 84°–86° C. and did not produce any depression of the melting point with the product prepared by Method C.

By Method A:

In the apparatus of Method C, 47 g (0.5 mole) of anyhdrous phenol was dissolved in 50 ml of absolute benzene; 39.6 g=40.3 ml (0.5 mole) of anhydrous pyridine was added, the mixture was raised to a temperature between 50° and 60° C., and at the same time 95 g (0.5 mole) of p-chloromethylbenzoyl chloride was added, drop by drop, over a period of one hour, with stirring and the exclusion of moisture. After about half of the chloromethylbenzoyl chloride had been added, the precipitation of pyridine hydrochloride began. After the addition of all of the acid chloride, stirring was continued for 1 hour at 60° C.

The cooled reaction mixture was freed of the pyridine hydrochloride by filtration, and the latter was thoroughly washed with benzene. The benzene was distilled out of the clear, pale brownish filtrate. The residue, 118 g (96%), crystallized after standing a while, to nearly colorless crystals of a melting point of 74° to 82° C. After re-crystallization from 1.7 liters of cyclohexane, the melting point was 85° to 87° C.

EXAMPLE 2 o-Chloromethylbenzoic acid phenyl ester

The ester was prepared by Method C only, by dissolving 47 g (0.5 mole) of phenol in 60 ml of benzene in the apparatus used in the preparation of the para compound, adding 0.5 ml of absolute pyridine as catalyst, and then adding 95 g (0.5 mole) of undiluted o-chloromethylbenzoyl chloride drop by drop at 55° to 60° C. over a period of about 1 hour, the mixture being stirred for another 4 hours at the refluxing temperature to complete the reaction. The benzene was then distilled out of the clear, light red solution thus obtained. The viscous oily, clear, red residue obtained in a quantitative yield crystallized after standing for a while at −15° C. The crystal mass thus obtained was ground in a chilled mortar with about 100 ml of intensely cooled isopropanol; the undissolved portion was removed by suction filtering and washed with 100 ml of isopropanol chilled to −20° C. After drying, 87 g (70%) was obtained of a colorless crystallizate with a melting point of 39°–41° C. For the analysis, 15 g was dissolved at 35° C. in 125 ml of isopropanol and set aside to crystallize at −20° C. 12.7 g of colorless needles was obtained with a melting point of 39°–41° C.

Elemental analysis: $C_{14}H_{11}ClO_2$ (Mol. Wt.=246.7).
Calculated: C 68.17%; H 4.49%; Cl 14.37%; O 12.97%.
Found: C 67.89%; H 4.35%; Cl 14.11%; O 13.26%.

EXAMPLE 3 p-Chloromethylbenzoicacid-4-methoxyphenylester

By Method C:

In the apparatus previously described, 62.1 g (0.5 mole) of hydroquinone monomethyl ether was dissolved in 100 ml of benzene, 0.5 ml of absolute pyridine was added to the solution, and a solution of 95 g (0.5 mole) of p-chloromethylbenzoyl chloride in 80 ml of benzene was added, drop by drop, over a period of 30 minutes, at 50°–55° C. Then the mixture was refluxed for 5 hours, after which the benzene was distilled out. 138 g (100%) was obtained of a dark brown oil which upon cooling solidified into gray-green, flake-like crystals. M.P. 78°–86.5° C. This product was recrystallized from 2.8 liters of cyclohexane, a small amount of a dark green oil remaining undissolved. Thereafter the substance was in pale gray flakes with a melting point of 88°–91° C. By concentrating the mother liquor, 88% of the amount put in was isolated. For the analysis, 20 g was again recrystallized from 400 ml of cyclohexane with the addition of animal charcoal.

Colorless flakes, melting point 88.5°–91.5° C.

Elemental analysis: $C_{15}H_{13}ClO_3$ (Mol. Wt.=276.73).
Calculated: C 65.11%; H 4.74%; Cl 12.81%; O 17.34%.
Found: C 64.97%; H 4.59%; Cl 12.61%; O 17.52%.

The infrared and NMR spectra are in complete accord with the structure for p-chloromethylbenzoicacid-4-methoxyphenyl ester.

By Method B:

As previously described, 24.85 g (0.2 mole) of hydroquinone monomethyl ether was dissolved at room temperature in 200 ml of 1 N NaOH and this strongly brown-colored solution was reacted at 20°-25° C. with 38 g (0.2 mole) of p-chloromethylbenzoyl chloride. After the addition of all of the acid chloride the mixture was stirred for another hour. The precipitated, dark brown reaction product was suction filtered, washed with water and dried. 47.5 g of raw product was obtained (85%), which was recrystallized as described above. The melting point was then 86°-89° C. No melting point depression with the preparation made by Method C.

EXAMPLE 4 p-Chloromethylbenzoicacid-α-napthyl ester 72.1 g (0.5 mole) of α-naphthol was heated to 50° C. with 150 ml of benzene and 0.5 ml of N-methylpyrrolidine, whereupon a clear solution was obtained. Following the procedure of Method C, 95 g (0.5 mole) of p-chloromethylbenzoyl chloride dissolved in 80 ml of benzene was added drop by drop over a period of about 30 minutes, and then the mixture was refluxed for 5 hours under a weak current of nitrogen gas. The benzene was then distilled from the clear, orange-colored solution. The residue crystallized upon cooling to a yellow mass amounting to 148 g (100%), M.P. 93°-96° C. The entire amount of the raw product was recrystallized from 3 liters of cyclohexane with the addition of decolorizing carbon. About 80% of the material put in was obtained in light yellow needles of a melting point of 104°-106° C. For the analysis, 20 g was again recrystallized from 400 ml of cyclohexane. 16.5 g of very pale yellow needles was obtained, M.P. 105°-106.5° C.

Elemental Analysis: $C_{18}H_{13}ClO_2$ (Mol. Wt. 296.76).
Calculated: C 72.85%; H 4.42%; Cl 11.95%; O 10.78%.
Found: C 72.63%; H 4.29%; Cl 11.79%; O 11.01%.

The infrared and NMR spectra are in accord with the structure.

EXAMPLE 5 p-Chloromethylbenzoicacid-β-naphthylester

This ester was prepared by Method C by placing 72.1 g (0.5 mole) of β-naphthol, suspended in 150 ml of benzene, and 0.5 ml of pyridine in the vessel, adding all at once, at room temperature, a solution of 95 g (0.5 mole) of p-chloromethylbenzoyl chloride in 80 ml of benzene, and refluxing this reaction mixture for 6 hours, while passing a weak current of nitrogen through the apparatus. The HCl cleavage began at about 40° C., and at an internal temperature of 50° C., a clear, homogeneous solution had formed. After the end of the reaction time the benzene was substantially removed by distillation. The residue crystallized to a grayish pink crystal mass, the yield of which was quantitative (147.5 g). The raw ester melted at 90°-96° C. It was recrystallized from 2.5 liters of isopropanol with the addition of decolorizing carbon, yielding colorless, pearly, shiny flakes of a melting point of 102°-103.5° C.

Elemental Analysis: $C_{18}H_{13}ClO_2$ (Mol. Wt. 296.76).
Calculated: C 72.85%; H 4.42%; Cl 11.95%; O 10.78%.
Found: C 72.79%; H 4.29%; Cl 11.77%; O 11.01%.

EXAMPLE 6 o-Chloromethylbenzoicacid-β-naphthylester

The preparation was similar to that of the para compound as described in Example 5, the following quantities being used:
72.1 g (0.5 mole) of β-naphthol
95.0 g (0.5 mole) of o-chloromethylbenzoyl chloride
330 ml of absolute benzene, and
0.5 ml of absolute pyridine.

All of the substances were combined at room temperature and refluxed in a weak current of nitrogen with the exclusion of moisture, for four to five hours. The HCl evolution began at about 40° C. and at 50° C. a clear, homogeneous mixture was obtained.

Purification was accomplished by distilling out the benzene, a vacuum being applied at the end. We obtained a nearly black, thick, oil residue which crystallized upon cooling to room temperature. The raw product was ground in 250 ml of isopropanol and the then yellowish crystallizate was suction filtered and dried. 119 grams, corresponding to a yield of 80%, were obtained, with a melting point of 64°-66° C. The entire quantity was recrystallized from 1.8 liters of isopropanol with the addition of decolorizing carbon, yielding 109 grams of a melting point of 65° to 67.5° C. A specimen was again recrystallized for the analysis. The melting point was then 66°-68° C.

Elemental analysis: $C_{18}H_{13}ClO_2$ (Mol. Wt. 296.76).
Calculated: C 72.85%; H 4.42%; Cl 11.95%; O 10.78%.
Found: C 72.69%; H 4.29%; Cl 12.08%; O 10.90%.

EXAMPLE 7 p-Chloromethylbenzoicacid-p-tert.-butylphenyl ester

In the apparatus of Method C, the following were mixed together cold and refluxed in a weak current of nitrogen for 6½ hours with the exclusion of moisture:
75.1 g (0.5 mole) of p-tert.-butylphenol
95.0 g (0.5 mole) of p-chloromethylbenzoyl chloride
180 ml of benzene, and
0.5 ml of pyridine.

Then the benzene was distilled out of the reaction mixture. The yellow, oily residue crystallized upon cooling after standing a while. 151 g (100%) was obtained of a raw crystallizate having a melting point of 73°-82° C., which was recrystallized from 900 ml of cyclohexane. 5.2 g of chloromethylbenzoic acid remained undissolved, having a melting point of 197°-199° C., which was filtered out.

The ester melted at 83°-86° C. after recrystallization. 15 g was again recrystallized from 300 ml of petroleum ether (B.P. 40°-60° C.). The boiling point was then 86.5°-87.5° C.

Elemental analysis: $C_{18}H_{19}ClO_2$ (Mol. wt. 302.80).
Calculated: C 71.40%; H 6.32%; Cl 11.71%; O 10.57%.
Found: C 71.30%; H 6.39%; Cl 11.57%; O 10.79%.

EXAMPLE 8 p-Chloromethylbenzoicacid-4-benzylhydroxyphenyl ester:

As above, the following were refluxed for 7 hours in a weak current of nitrogen gas:
20.02 g (0.1 mole) of hydroquinonemonobenzyl ether (M.P. 119° C.)
18.90 g (0.1 mole) of p-chloromethylbenzoyl chloride
150 ml of anhydrous toluene, and 0.2 ml of absolute pyridine.

A clear, yellow-brownish solution was obtained from which most of the ester crystallized upon cooling. 25.6 g of raw crystallizate (72%) of a melting point of 125°–129° C. was obtained. The yield was increased to 84% by concentrating the mother liquor.

The raw crystallizate was recrystallized from toluene in a ratio of 1:14. We obtained pearly, shiny, colorless, small flakes with a melting point of 136.5°–139° C. Another recrystallization did not change the melting point.

Elemental analysis: $C_{21}H_{17}ClO_3$ (Mol.wt. 352.82). Calculated: C 71.49; 1%; H 4.85%; Cl 10.06%; O 13.60%. Found: C 71.27%; H 4.90%; Cl 9.93%; O 13.86%.

EXAMPLE 9 p-Chloromethylbenzoicacid-p-cumylphenyl ester

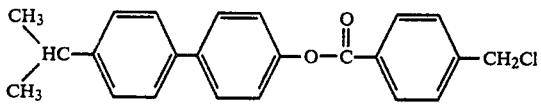

In the experimental apparatus previously described, the following were refluxed until the evolution of HCl had substantially stopped (about 7–8 hours):
31.23 g (0.1 mole) of p-cumylphenol
100 ml benzine (B.P. 80°–100° C.)
18.9 g (0.1 mole) of p-chloromethylbenzoyl chloride
0.1 ml of N-methylpyrrolidine.

Then the yellowish brown, somewhat turbid reaction solution, cooled to room temperature, was filtered and the benzine was removed by vacuum distillation. The remaining brownish, oily residue was then held under an oil pump vacuum (0.4–0.5 mm Hg) in a 225° C. oil bath for the removal of other volatile components, until no more condensate passed over.

In this manner about 2 g of a product passing over between 115° and 150° C. at 0.4 mm Hg was removed.

The thick oily brown residue then remaining crystallized completely but very slowly after several days of standing at room temperature. Yield: 33.2 g (91%), M.P. 56°–60° C. After recrystallization from petroleum ether the melting point was 62.5° to 63.5° C.

Elemental analysis: $C_{23}H_{21}ClO$ (Mol.Wt. 364.88). Calculated: C 75.81%; H 5.80%; Cl 9.72%; O 8.77%. Found: C 75.55%; H 5.75%; Cl 9.48%; O 8.93%.

The same result was obtained when the above amounts of the starting substances were boiled in the presence of 0.1 ml of absolute pyridine in 100ml of xylene. The reaction time then amounted to only 5 hours.

EXAMPLE 10 p-Chloromethylbenzoicacid-p-nitrophenyl ester:

For the preparation of this ester, the following were refluxed until the evolution of HCl had stopped (about 5 hours):
27.82 g (0.2 mole) of p-nitrophenol
37.82 g (0.2 mole) of p-chloromethylbenzoyl chloride
100 ml of absolute xylene and
0.2 ml of tri-n-butylamine.

When the reaction mixture cooled, part of the ester crystallized out in the form of gray flakes which, after suction filtration and drying, melted at 110°–114.5° C. Concentration of the mother liquor yielded additional crystallizate. In all, 53 g was obtained, corresponding to a 91% yield. For refinement, the product was recrystallized from xylene in a 1:6.25 ratio. The melting point was then 118°–119.5° C. Additional recrystallization did not increase the melting point.

Elemental Analysis: $C_{14}H_{10}ClNO_4$ (Mol. wt. 291.69). Calculated: C 57.65%; H 3.46%; Cl 12.15%; N 4.80%; O 21.94%. Found: C 57.54%; H 3.21%; Cl 12.18%; N 4.80%; O 22.26%.

EXAMPLE 11

4-Chloromethylbenzoicacid-8-oxyquinoline ester

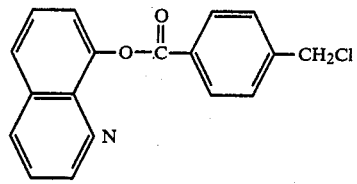

This ester was prepared by Method A as follows: 10.79 g (0.075 mole) of 8-hydroxyquinoline was dissolved in 30 ml of anhydrous tetrahydrofuran at room temperature, 7.59 g=10.35 ml (0.075 mole) of anhydrous triethylamine is added, and then, with stirring, a solution of 14.18 g (0.075 mole) of p-chloromethylbenzoyl chloride in 50 ml of absolute tetrahydrofuran was added drop by drop such that the temperature of the reaction mixture did not increase above 30° C. The reaction is very exothermic and amine hydrochloride immediately precipitates. After all of the chloromethylbenzyl chloride solution had been added, the mixture was stirred for 1 hour at 30° C. to complete the reaction.

For refinement, the reaction mixture was stirred into 400 ml of water, the precipitated, colorless ester was suction filtered and washed with water, and was then dried in vacuo at 50° to 80° C. Yield 21.75 g (97.5%), M.P. 141°–143° C.

Recrystallization from toluene in a ratio of 1:8.5 yielded colorless needles of M.P. 144°–145° C. Another recrystallization from isopropanol (ratio 1:30) did not change the melting point of 144°–145° C.

Elemental analysis: $C_{17}H_{12}ClNO_2$ (Mol. wt. 297.75). Calculated: C 68.58%; H 4.06%; Cl 11.87%; N 4.71%; O 10.75%. Found: C 68.77%; H 3.95%; Cl 12.01%; N 4.83%; O 10.55%.

The infrared spectrum and NMR spectrum confirm the above-given structure.

EXAMPLE 12

4-Chloromethylbenzoicacid-(2,4-dichloro-6-methylphenyl) ester

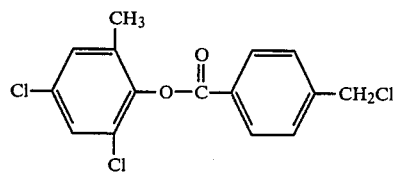

88.5 g (0.5 mole) of 2,4-dichloro-6-methylphenol, 180 ml of dry xylene, 95 g (0.5 mole) of p-chloromethylbenzoyl chloride and 0.5 ml of pyridine were refluxed for 24 hours in a weak current of nitrogen with the exclusion of moisture. After cooling, the slightly turbid (pyridine hydrochloride), orange-colored solution was filtered free of a small amount of a blackish brown resin, and the filtrate was freed of xylene at diminished pressure. The residue (165 g=100%) crystallized after two days of standing to a light brown crystal mass, which was triturated in 200 ml of ice-cold petroleum ether and suction filtered. After drying, nearly colorless crystals were obtained with a melting point of 71°-73° C. Recrystallization from petroleum ether (1:10) yielded white needles melting at 74°-75° C.; no change in the melting point was brought about by repeated recrystallization.

Elemental analysis: $C_{15}H_{11}Cl_3O_2$ (Mol. wt. 329.62). Calculated: C 54.66%; H 3.36%; Cl 32.27%; O 9.71%. Found: C 54.71%; H 3.28%; Cl 32.11%; O 9.89%.

EXAMPLE 13

4-Chloromethylbenzoicacid-(2,4-dichlorophenyl) ester 81.5 g (0.5 mole) of 2,4-dichlorophenol was dissolved in 100 ml of absolute xylene, mixed with a solution of 95 g (0.5 mole) of p-chloromethylbenzoyl chloride in 80 ml of xylene, and after the addition of 0.5 ml of N-methylpyrrolidine the mixture was refluxed for 6 to 7 hours in a weak current of nitrogen.

After the reaction has ended the mixture was allowed to cool, part of the ester crystallizing in colorless crystals. Additional ester was isolated by concentrating the filtrate. The yield of raw ester melting at 86° to 90° C. was 137 grams (87.0%). When recrystallized from cyclohexane (1:10), the substrate melted at 91.5° to 92.5° C.

Elemental Analysis: $C_{14}H_9Cl_3O_2$ (Mol.Wt.: 315.58). Calculated: C 53.29%; H 2.87%; Cl 33.70%; O 10.14%. Found: C 53.44%; H 2.71%; Cl 33.82%; O 10.31%.

EXAMPLE 14

4-Chloromethylbenzoic acid-(2,4,6-trichlorophenyl) ester

In the manner described above,
98.8 g (0.5 mole) of 2,4,6-trichlorophenol,
150 ml of dry xylene,
95 g (0.5 mole) of p-chloromethylbenzoyl chloride and
0.5 ml of absolute pyridine
were refluxed in a weak current of nitrogen for 9 hours. The product which crystallized out of the reaction mixture upon cooling was suction filtered and the filtrate was concentrated by evaporation. We obtained 148 g (85%) melting at 97°-99° C. 20 g of raw ester was recrystallized from 300 ml of isopropanol. The melting point was then 99.5° to 100.5° C. Further recrystallization produced no further increases in the melting point.

Elemental analysis: $C_{14}H_8Cl_4O_2$ (Mol. Wt. 350.02). Calculated: C 48.04%; H 2.30%; Cl 40.51%; O 9.14%. Found: C 48.17%; H 2.16%; Cl 40.54%; O 8.94%.

EXAMPLE 15

4-Chloromethylbenzoicacid-(2,3,4,6-tetrachlorophenyl) ester 58 g (0.25 mole) of 2,3,4,6-tetrachlorophenol, 100 ml of absolute xylene, 47.5 g (0.25 mole) of p-chloromethylbenzoyl chloride and 0.25 ml of absolute pyridine were refluxed as described above for 4 hours. A part of the ester that formed crystallized upon the cooling of the reaction solution. The concentrated mother liquor yielded much additional crystallizate. In all, 93.15 g (97%) was isolated, with a melting point of 110° to 114° C. The raw ester was recrystallized from cyclohexane (1:15) and then melted at 143°-149° C. Another recrystallization raised the melting point to 150°-152° C.

Elemental Analysis: $C_{14}H_7Cl_5O_2$ (Mol. Wt. 384.47). Calculated: C 43.73%; H 1.84%; Cl 46.11%; O 8.32%. Found: C 43.61%; H 1.68%; Cl 45.99%; O 8.19%.

EXAMPLE 16

4-Chloromethylbenzoicacid-(2,3,4,5,6-pentachlorophenyl) ester 133.2 g (0.5 mole) of pentachlorophenol, 330 ml of absolute xylene, 95 g (0.5 mols) of p-chloromethylbenzoyl chloride and 0.5 ml of pyridine were refluxed for about 6 hours as described above.

At the end of the refluxing we let the mixture cool, and crystallization commenced when the temperature of the reaction was at about 80° C. After several hours of standing at room temperature, the mixture was suction filtered. 177 g (84.5%) Of raw ester melting at 178°-179° C. was obtained. The mixed melting point with pentachlorophenol was 130° C. By concentrating the filtrate of the initial crystallization another 15.5 g of ester melting at 172°-174° C. was obtained, which correspond to a total yield of 91.8%. 20 g of raw ester was recrystallized from 160 ml of xylene. The melting point was then 179°-180° C. Further recrystallization brought no further raising of the melting point.

Elemental analysis: $C_{14}H_6Cl_6O_2$ (Mol. Wt. 418.91). Calculated: C 40.14%; H 1.44%; Cl 50.78%; O 7.64%. Found: C 40.34%; H 1.37%; Cl 50.63%; O 7.68%.

EXAMPLE 17

4-Chloromethylbenzoicacid-(2,4,6-tribromophenyl) ester

In the manner described above,
165.5 g (0.5 mole) of 2,4,6-tribromophenol,
330 ml of absolute xylene,
95 g (0.5 mole) of p-chloromethylbenzoyl chloride, and
0.5 ml of N-methylpyrrolidine
were refluxed in a weak current of nitrogen for 24 hours with the exclusion of moisture. The xylene was then removed from the reaction solution by distillation, using a water jet vacuum at the end. The yellowish brown, oily residue crystallized after standing a while. 239 g Of raw product was obtained (99% yield). The raw product was ground with 200 ml of cyclohexane and suction filtered and dried, yielding 198 g (=82%) of nearly colorless crystallizate melting at 106° to 111° C. When it was recrystallized from cyclohexane in a 1:10 ratio we obtained coarse, cubic crystals melting at 114°-115° C. Further recrystallization did not change the melting point.

Elemental analysis: $C_{14}H_8Br_3ClO_2$ (Mol. Wt. 483.4). Calculated: C 34.79%; H 1.67%; Br 49.59%; Cl 7.33%; O 6.62%. Found: C 34.98%; H 1.55%; Br 49.34%; Cl 7.20%; O 6.84%.

EXAMPLE 18

4-Chloromethylbenzoicacid-(2,3,4,5,6-pentabromophenyl) ester

As in Example 17, the following substances and quantities were reacted:
244.5 g (0.5 mole) of pentabromophenol,
360 ml of absolute xylene,
95 g (0.5 mole) of p-chloromethylbenzoyl chloride and
0.5 ml of pyridine.
The mixture was refluxed for 7 to 8 hours.

The ester that formed was poorly soluble in cold xylene and crystallized substantially upon cooling. We obtained as the first crystallizate 289 g (90%) of light yellow crystals melting at 216°–218.5° C. The mixed melting point with pentabromophenol was 168°–175° C. When the substance was recrystallized from xylene in a ratio of 1:10, a melting point of 218.5°–220° C. was obtained. Further recrystallization did not alter the melting point.

Elemental analysis: $C_{14}H_6Br_5ClO_2$ (Mol. wt. 641.2). Calculated: C 26.22%; H 0.94%; Br 62.31%; Cl 5.52%; O 4.99%. Found: C 26.18%; H 0.83%; Br 62.70%; Cl 5.15%; O 5.08%.

If the experiment is performed with dimethylacetamide (0.5 ml) instead of pyridine as catalyst, about 50 hours of refluxing were required to complete the reaction.

EXAMPLE 19 p-Chloromethylbenzoicacid-(4-chlorophenyl)-thiol ester

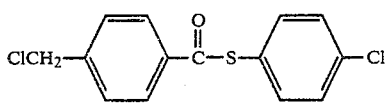

In the manner described above,
29 g (0.20 mole) of p-chlorothiophenol,
100 ml of dry toluene
38.0 g (0.20 mole) of p-chloromethylbenzoyl chloride and
0.2 ml of absolute pyridine
were refluxed for 4 hours with the exclusion of moisture. The formation of HCl began at 60° C. (in the reaction mixture) and had ended by the end of the 4 hours.

When the light yellow reaction solution cooled, a small portion (20.2 g) of the thiol ester had already crystallized Another 36.9 g of crystallizate was obtained by concentrating the mother liquor in the water jet vacuum to the dry state. Total yield 57.1 g (96.3%). The first crystallizate melted at 105°–107° C., and the concentrate at 98° to 102.5° C.

20 g of the first crystallizate, recrystallized from 400 ml of cyclohexane, yielded an ester in the form of colorless, odorless needles melting at 106°–107.5° C.

Elemental analysis: C H Cl OS (Mol. wt. 297.2). Calculated: C 56.58%; H 3.39%; Cl 23.86%; O 5.38%; S 10.79%. Found: C 56.36%; H 3.19%; Cl 23.62%; O 5.04%; S 10.67%.
Infrared and NMR spectra are entirely in accord with the structure.

EXAMPLE 20

4-Chloromethylbenzoic acid phenylthiol ester

In the manner described in Example 19,
22.03 g=20.5 ml (0.2 mole) of thiophenol,
100 ml of dry toluene,
38 g (0.2 mole) of p-chloromethylbenzoyl chloride and
0.2 ml of absolute pyridine
were refluxed for 4 hours with the exclusion of moisture. In the subsequent cooling to room temperature a small part of the ester (12.6 g, M.P. 90°–93° C.) had already crystallized out. The mother liquor was reduced to the dry state in vacuo, whereupon we isolated another 38.3 grams melting at 90°–93° C. The total yield was thus 96.5%.

When the substance was recrystallized from cyclohexane 1:15, we obtained a pure crystallizate with a melting point of 92°–93° C. Further recrystallization did not raise the melting point any further.

The infrared and NMR spectra confirm the structure of a chloromethyltionbenzoic acid phenyl ester.

Elemental analysis: $C_{14}H_{11}OSCl$ (Mol. wt. 262.75). Calculated: C 63.86%; H 4.07%; O 6.23%; S 12.14%; Cl 13.34%. Found: C 64.00%; H 4.22%; O 6.09%; S 12.20%; Cl 13.49%.

EXAMPLE 21

4,4'-Dihydroxydiphenylsulfone-bis-0,0-(4-chloromethylbenzoic acid) ester

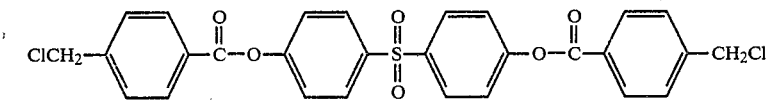

Using a stoichiometric amount of triethylamine (Method A), we synthesized the substance as follows: 125 g (0.5 mole) of sulfonyl diphenol (M.P. 239°–242° C.) was dissolved in 750 ml of anhydrous tetrahydrofuran, and 140 ml of absolute triethylamine (1 mole) was added. The mixture was heated to 50° C. and then, with stirring and the exclusion of moisture, a solution of 189.05 g (1 mole) of p-chloromethylbenzoyl chloride in 325 ml of absolute tetrahydrofuran was added drop by drop over a period of 60 minutes. The temperature of the reaction mixture rose to about 60° C. and aminohydrochloride precipitated. Stirring was continued for 1 hour at 60° C. and then the mixture was cooled to room temperature and stirred into 2.5 liters of cold water. The colorless precipitate that formed was suction filtered and washed with 3 liters of water until the filtrate was chloride-free. After drying, 264 g (95%) of ester remained with a melting point of 172°–174.5° C. When recrystallized from acetone (1:15), the melting point became 178°–179° C.

Elemental Analysis: $C_{28}H_{20}Cl_2O_6S$ (Mol. wt. 555.44). Calculated: C 60.55%; H 3.60%; Cl 12.78%; O 17.30%; S 5.77%. Found: C 60.84%; H 3.40%; Cl 12.49%; O 17.22%; S 5.62%.

The structure given above was completely confirmed by the infrared and NMR spectra.

---

Correlation:
ν C = 0 (aromatic ester): 1715 cm$^{-1}$
ν C = 0 (aromatic ester): 1245 cm$^{-1}$
ν SO$_2$ (asym./s.m.): 1270–1240 cm$^{-1}$
1090–1135 cm$^{-1}$

|  |  | Number of protons according to integration: |
|---|---|---|
| CH₂Cl | d = 4.62 ppm Singlet | 3.9 |
| SO₂-C₆H₄—O | AB System (I$_{AB}$ ~ 9 Hz) centered at d = 7.7 ppm) | 16.2 |
| OCC-C₆H₄—CH₂Cl | AB System (I$_{AB}$ ~ 8 Hz) centered at d = 7.84 ppm |  |

EXAMPLE 22

4,4'-Dihydroxydiphenylsulfide-bis-O,O-(4-chloromethylbenzoic acid) ester

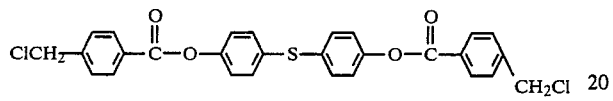

In a manner similar to Example 21, 54.6 g (0.25 mole) of thiodiphenol, M.P. 146°–147° C., was dissolved in 250 ml of absolute tetrahydrofuran; 50.6 g=69 ml (0.5 mole) of anhydrous triethylamine was added to the solution, which was heated to 50° C., and a solution of 95 g (0.5 mole) of p-chloromethylbenzoyl chloride in 150 ml of absolute tetrahydrofuran was added drop by drop over a period of one hour with stirring and the exclusion of moisture. Amine salt immediately precipitated. After the addition of all the acid chloride, stirring was continued for 1 hour at 55°–60° C. The reaction mixture, cooled to room temperature, was stirred into about 2 liters of cold water; the colorless ester that precipitated was removed by suction filtering, and was washed with water until free of chloride. After drying, the yield was 128 g (97.7%), M.P. 134°–139° C. When this was recrystallized from xylene (1:12) we obtained colorless needles melting at 143°–145° C., whose melting point was not raised further by additional recrystallization.

Elemental Analysis: C₂₈H₂₀Cl₂O₄S (Molecular weight 523.44). Calc.: C 64.25%; H 3.85%; Cl 13.55%; O 12.23%; S 6.13%. Found: C 64.08%; H 3.59%; Cl 13.41%; O 12.39%; S 6.19%.

EXAMPLE 23

2,2-Diphenylpropane-bis-4,4'-(2-chloromethylbenzoic acid) ester

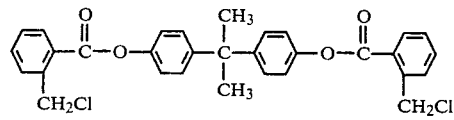

In the apparatus previously described,
57.1 g (0.25 mole) of 4,4'-dihydroxy-(2,2-diphenylpropane),
150 ml of anhydrous xylene,
94.55 g (0.5 mole) of o-chloromethylbenzoic acid chloride, and
0.25 ml of absolute pyridine
were first allowed to react for 45 minutes at 120° C. (strong formation of HCl), and then refluxed for another 5 hours.

Then the xylene was vacuum distilled from the reddish, clear reaction mixture.

We obtained 132.5 g (99%) of a light brown residue which crystallized after standing a while. Melting point of the raw ester: 108° to 114.5° C.

Upon recrystallization from 800 ml of ethylene glycol monomethyl ether, 103 g of yellowish crystals were obtained which melted at 115°–116.5° C. Repeated recrystallization produced no further change in the melting point.

Elemental Analysis: C₃₁H₂₆Cl₂O₄ (Mol. wt.: 533.46;. Calc.: C 69.80%; H 4.91%; Cl 13.29%; O 12.00%. Found: C 69.66%; H 4.69%; Cl 13.02%; O 12.19%.

The infrared and NMR spectra completely confirm the presence of a bisester of the above formula. No signs of large amounts of impurities were observed.

EXAMPLE 24

(3,3',5,5'-Tetrabromo-2,2-diphenylpropane)-4,4'-bis-(2-chloromethylbenzoic acid ester)

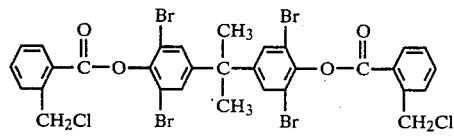

In the manner described in Example 23,
108.8 g (0.2 mole) of tetrabromo-bisphenol A,
150 ml of absolute xylene
75.65 g (0.4 mole) of o-chloromethylbenzoyl chloride and
0.2 ml of anhydrous pyridine
were refluxed for 23 hours. At an internal temperature of 70° C. the formation of HCl began.

The clear, orange-colored reaction solution was freed of xylene in vacuo, and a light brown, clear, syrupy liquid remained (180 g) which was dissolved in 1.2 liters of hot ethylene glycol monomethyl ether and brought to crystallization. We obtained 136 g (82%) of virtually colorless flakes which melted at 164°–167° C. For further refinement 5 grams of substance were recrystallized again from 30 ml of methyl glycol. The melting point was then 168°–170° C.

Elemental Analysis: C₃₁H₂₂Br₄Cl₂O₄ (mol. wt. 849.07). Calc.: C 43.85%; H 2.61%; Br 37.65%; Cl 8.35%; O 7.54%. Found: C 43.63%; H 2.60%; Br 37.74%; Cl 8.30%; O 7.37%.

The infrared and NMR spectra unequivocally confirm the presence of a bisester of the above structure.

EXAMPLE 25 (Use)

This example shows the variety of ways in which the —CH₂—Cl grouping of the above-described esters can be subjected to further reactions.

(a) The replacement of the Cl atom of the CH₂Cl group with a bromine atom was accomplished with the ester of Example 17, for example, as follows: 48.35 g (0.1 mole) of 4-chloromethylbenzoicacid-(2,4,6-tribromophenyl) ester was dissolved at 40° C. in 200 ml of acetone and mixed at this temperature with a solution of 12 g of sodium bromide (0.115 mole) in 20 ml of water. The mixture was then refluxed for 6 hours.

The 4-bromomethylbenzoic acid-(2,4,6-tribromophenyl) ester precipitated as a crystallizate upon the cooling of the reaction mixture. The crystallizate was suction filtered, washed with water (to remove sodium chloride and excess NaBr) and dried. 40 g (75.5 wt.-%) with a melting point of 109°-113° C. was obtained. This was recrystallized from 320 ml of cyclohexane, and the melting point was then 122° to 124° C. The mixed melting point with the starting material was 109° to 112° C.

Elemental analysis: $C_{14}H_8Br_4O_2$ (Mol. wt. 527.90). Calc.: C 31.86%; H 1.53%; Br 60.55%; O 6.06%. Found: C 32.02%; H 1.48%; Br 60.39%; O 6.14%.

(b) Preparation of the pentabromophenyl ether of 4-hydroxymethylpentabromophenylbenzoate

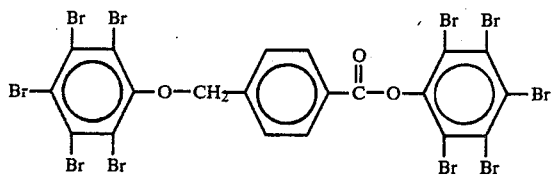

For this purpose, 6.41 g (0.01 mole) of 4-chloromethyl-benzoic acid-(2,3,4,5,6-pentabromophenyl) ester of Example 18 was stirred into a 75° C. solution of 0.4 g (0.01 mole) of sodium hydroxide and 4.90 g (0.01 mole) of pentabromophenol in 150 ml of ethylene glycol monomethyl ether, and this mixture was refluxed for 30 minutes with stirring. The compound of the above structure precipitated while the solution was still hot. It was removed by suction filtration after cooling, washed on the filter funnel first with a small amount of methanol and then with water until the filtrate was free of chloride, and dried.

The yield was 8.6 g (78 wt.-%) melting at 286°-289° C., after sintering beginning at 278° C.

When the product was recrystallized from 1 liter of boiling xylene the melting point was 297°-299° C.

Elemental Analysis: $C_{20}H_6Br_{10}O_3$ (mol. Wt. 1093.36). Calc.: C 21.97%; H 0.55%; Br 73.09%; O 4.39%. Found: C 21.83%; H 0.47%; Br 72.89%; O 4.51%.

The compound thus prepared can serve as an antimycotic additives, for example, on the basis of its high bromine content.

(c) Preparation of 4-(O,O-diethylophsphonatomethyl)benzoic acid-(2,4,6-tribromophenyl ester)

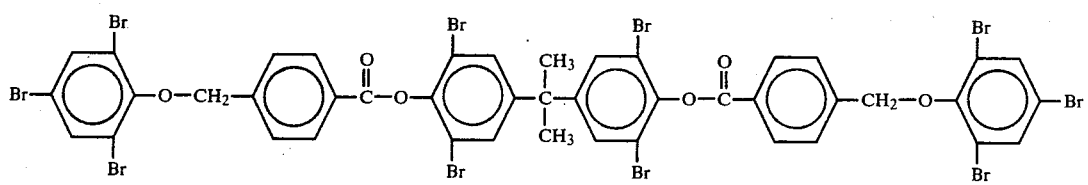

This compound was obtained from the 4-chloromethylbenzoic acid-(2,4,6-tribromophenyl) ester of Example 17 as follows:

96.7 g (0.2 mole) of p-chloromethylbenzoic acid tribromophenyl ester was mixed with 33.25 g (0.2 mole)=35 ml of triethylphosphite and refluxed in a 185° C. oil bath for 2 hours with the passage of a weak current of nitrogen over the mixture. After this period of time no reflux of triethylphosphite was to be ovserved in the reflux condenser and thus the splitting off of ethyl chloride had ended.

The reaction mixture was poured while still hot into a porcelain dish and the cooled, now sticky, resinous preparation was rubbed with petroleum ether, whereupon a nearly colorless, crystalline powder slowly formed, which after the evaporation of the petroleum ether weighed 109 g (93%) and had a melting temperature of 118°-129° C.

The product was recrystallized from about 4 liters of cyclohexane, and we obtained colorless crystals of a melting point of 135°-136° C. 10 grams recrystallized again from 400 ml of cyclohexane yielded a crystallizate of unchanged melting point.

Elemental analysis: $C_{18}H_{24}Br_3PO_5$ (mol. wt. 585.05). Calc.: C 36.62%; H 4.08%; Br 40.60%; P 5.23%; O 13.54%. Found: C 36.72%; H 3.87%; Br 40.57%; P 5.26%; O 13.26%.

EXAMPLE 26

(a) Example 24 was repeated, but instead of o-chloromethylbenzoic acid chloride 0,4 mole of the p-compound was used in the reaction.

After recrystallization from methyl glycol the new compound 3.3',5.5' Tetrabromo-2,2-diphenylpropan)-4,4'-bis-(4-chloromethylbenzoic acid ester) in a yeald of 90.6%, Melting point (m.p.) 193°-199° C., was obtained.

EXAMPLE 27 (Use)

The product of example 26 was converted into (3,3',5,5'-Tetrabrom-2,2-diphenylpropan)-4,4'-bis-[p-(2,4,6-tribromophenoxymethyl)-benzoic-acid]-ester:

which is very useful as flame retardent.

Also the product of example 24 or isomeric mixtures i.e. mixtures of products of examples 24 and 26 have the same good flame retarding properties.

preparation:

In a three necked round flask of 500 ml volume, equipped with stirrer, reflux condenser and internal thermometer was filled the following mixture:

700 ml methyl glycol 9,6 g (=0,24 mole) solid sodium hydroxyde
73,4 g (=0,24 mole) tribromphenol and
101,9 g (=0,12 mole) of the substance of preceding example 26.

The reaction was effected by dissolving the solid alkali in the methyl glycol at 75° C. and then adding first the phenol and then adding under stirring the chlormethyl compound while heating up to boiling temperature. The product began to fall out. For completition of the reaction was stirred one more hour at boiling temperature under reflux.

The mixture was cooled and after crystallization the product was filtered and dried.

Yeald 153 g (90,6 wt.-%) of m.p. 193°-199° C.

EXAMPLE 28 (Use)

In corresponding manner as noted above in example 27, the product of example 18 was converted into 4-(2,4,6-trichlorphenoxymethyl) benzoic acid (penta-bromphenyl)-ester by reaction with 2,4,6-trichlor-phenol in presence of alcali hydroxide.

The yeald was 94 wt.-% of theoretical amount. Melting point 190°-194° C., recrystallized from methyl glycol 193°-195° C.

EXAMPLE 29 (Use)

Example 17 was repeated but o-chloromethylbenzoylchloride was used instead of the p-compound. The resulting compound was converted according the manner of example 27 into o-(pentabromophenoxymethyl)-benzoicacid-(2,4,6-tribromiophenyl)-ester, by reaction with alkali hydroxide and the equivalent of pentabromophenol.

Yeald 88,5 wt.-%. m.p. 277°-279° C.

EXAMPLE 30

The product of example 18 was convected into its pentabromphenylether ester by reaction with alkali and pentabromophenol under conditions as noted in example 27.

Yeald 85 wt.-%. m.p. 284°-289° C.

EXAMPLE 31

In corresponding manner was produced:
p-(2,4,6-tribromophenoxymethyl)-benzoic acid-(2.4.6-tribromophenyl)-ester of m.p. 183°-184,5° C.

EXAMPLE 32

In the followong table results of flame retarding test of the products according the invention incorporated in plastic materials are given.

The values of LOI-% O₂ are determined according ASTM-D 2863-70. The values mean the concentration of vol-% oxygen gas in that oxygen nitrogen mixture, which was just still able to effect burning under test conditions.

The higher the value of that oxygen-index, the better the flame retardent properties of the tested material will be. For purpose of comparison some conventional flame retartents of known good effect are additionally listed in the table. Nevertheless compounds produced from products according this invention are regarded superior.

| plastic | substance of example | added** substance | amount** Sb$_2$O$_3$ | LOI vol.-% O$_2$ |
|---|---|---|---|---|
| PE | octabromo | 9 g | 4 g | 27.2 |
| PE | diphenylether octabromo diphenyl | 12 g | 4 g | 27.3 |
| PE | — | 0 | 0 | 17.3 |
| PE | 27 | 9 g | 4 g | 26.5 |
| PE | 27 | 6 g | 3 g | 25.6 |
| PE | 28 | 9 g | 4 g | 27.3 |
| PE | 27 | 12 g | 4 g | 28.4 |
| PE | 29 | 9 g | 3 g | 27.6 |
| PE | 30 | 12 g | 4 g | 27.8 |
| PE | 30 | 6 g | 3 g | 26.4 |
| PE | 26 b | 12 g | 6 g | 28.3 |
| PE | 26 b | 9 g | 4 g | 27.3 |
| PE | 31 | 12 g | 4 g | 28.1 |
| PE | 31 | 9 g | 3 g | 27.7 |

*PE = polyethylene
**per 100 g of the polymer

What is claimed is:

1. A chloromethylbenzoic acid phenyl ester of the formula:

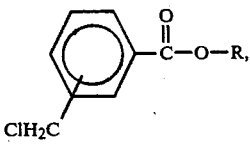

wherein the chloromethyl group is ortho or para and R is phenyl substituted by halogen or phenyl substituted by halogen and alkyl of 1 to 6 carbon atoms.

2. Ester of claim 1 which is 4-chloromethylbenzoic acid-(2,4-dichloro-6-methylphenyl) ester.

3. Ester of claim 1 which is 4-chloromethylbenzoic acid-(2,4-dichlorophenyl) ester.

4. Ester of claim 1, which is 4-chloromethylbenzoic acid-(2,4,6,-trichlorophenyl) ester.

5. Ester of claim 1, which is 4-chloromethylbenzoic acid-(2,3,4,6-tetrachlorophenyl) ester.

6. Ester of claim 1, which is 4-chloromethylbenzoic acid-(2,4,6, tribromophenyl) ester.

7. Ester of claim 1, which is 4-chloromethylbenzoic acid-(2,3,4,5,6-pentabromophenyl) ester.

8. A chloromethylbenzoic acid phenyl ester of the formula:

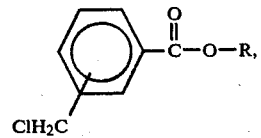

wherein the chloromethyl group is ortho or para, and R is of the formula:

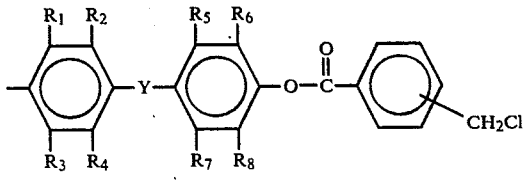

the chloromethyl group is ortho or para, and Y is alkyl of 1-4 carbon atoms, oxygen, sulfur, or SO₂, and R₁ to R₈ is each of the group hydrogen, alkyl of 1-6 carbon atoms, mononuclear aryl, benzyl, alkoxy of 1-4 carbon atoms, mononuclear aroxy, mononuclear aralkoxy, halogen and nitro.

* * * * *